United States Patent
Weng et al.

(10) Patent No.: US 8,755,871 B2
(45) Date of Patent: Jun. 17, 2014

(54) SYSTEMS AND METHODS FOR DETECTING ARRHYTHMIA FROM A PHYSIOLOGICAL SIGNAL

(75) Inventors: Binwei Weng, Boulder, CO (US); James Ochs, Seattle, WA (US)

(73) Assignee: Covidien LP, Mansfield, MA (US)

( * ) Notice: Subject to any disclaimer, the term of this patent is extended or adjusted under 35 U.S.C. 154(b) by 23 days.

(21) Appl. No.: 13/307,927

(22) Filed: Nov. 30, 2011

(65) Prior Publication Data

US 2013/0138002 A1    May 30, 2013

(51) Int. Cl.
*A61B 5/02* (2006.01)
*A61B 5/04* (2006.01)

(52) U.S. Cl.
USPC ............................. 600/509; 600/483; 600/515

(58) Field of Classification Search
USPC .......................................... 600/483, 509, 515
See application file for complete search history.

(56) References Cited

U.S. PATENT DOCUMENTS

| | | | |
|---|---|---|---|
| 5,092,341 A * | 3/1992 | Kelen | 600/515 |
| 5,188,108 A | 2/1993 | Secker | |
| 5,285,783 A | 2/1994 | Secker | |
| 5,285,784 A | 2/1994 | Seeker | |
| 5,368,026 A | 11/1994 | Swedlow et al. | |
| 5,398,682 A | 3/1995 | Lynn | |
| 5,558,096 A | 9/1996 | Palatnik | |
| 5,584,295 A | 12/1996 | Muller et al. | |
| 5,588,425 A | 12/1996 | Sackner et al. | |
| 5,605,151 A | 2/1997 | Lynn | |
| 5,862,805 A | 1/1999 | Nitzan | |
| 5,865,736 A | 2/1999 | Baker et al. | |
| 5,891,023 A | 4/1999 | Lynn | |
| 6,002,952 A | 12/1999 | Diab et al. | |
| 6,035,223 A | 3/2000 | Baker | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |

(Continued)

FOREIGN PATENT DOCUMENTS

| | | |
|---|---|---|
| EP | 0072601 A1 | 2/1983 |
| EP | 1344488 A2 | 9/2004 |

(Continued)

OTHER PUBLICATIONS

Stagg and Gennser, "Electronic analysis of foetal breathing movements: A practical application of phase-locked-loop principles," Journal of Med. Eng. and Tech., Sep. 1978, vol. 2, No. 5, pp. 246-249.

(Continued)

*Primary Examiner* — Nicole F Lavert
(74) *Attorney, Agent, or Firm* — Shvarts & Leiz LLP

(57) ABSTRACT

Arrhythmia may impact the determination of physiological information from a physiological signal. A patient monitoring system may detect the presence of arrhythmia based on changes in the physiological signal. Derived value data sets may be extracted from the physiological signal and calculations performed to generate arrhythmia features. The arrhythmia features may be used to generate an arrhythmia indicator that may indicate the presence of arrhythmia in the physiological signal.

19 Claims, 9 Drawing Sheets

(56) References Cited

U.S. PATENT DOCUMENTS

| | | |
|---|---|---|
| 6,325,761 B1 | 12/2001 | Jay |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Ali et al. |
| 6,609,016 B1 | 8/2003 | Lynn |
| 6,684,090 B2 | 1/2004 | Al-Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 | 6/2004 | Mannheimer |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El-Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 | 4/2008 | Al-Ali |
| 7,367,339 B2 | 5/2008 | Bickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 | 3/2009 | Weber et al. |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,801,591 B1 | 9/2010 | Shusterman |
| 7,869,980 B2 | 1/2011 | Casler et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 | 10/2011 | Al-Ali et al. |
| 8,130,105 B2 | 3/2012 | Al-Ali et al. |
| 8,203,438 B2 | 6/2012 | Kiani et al. |
| 8,275,553 B2 | 9/2012 | Amundson et al. |
| 8,364,226 B2 | 1/2013 | Diab et al. |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0222502 A1 | 10/2005 | Cooper |
| 2005/0222503 A1 | 10/2005 | Dunlop et al. |
| 2006/0122476 A1 | 6/2006 | Van Slyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0258921 A1 | 11/2006 | Addison et al. |
| 2007/0004977 A1 | 1/2007 | Norris |
| 2007/0010723 A1 | 1/2007 | Uutela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0179369 A1 | 8/2007 | Baker |
| 2007/0213619 A1 | 9/2007 | Linder |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0077022 A1 | 3/2008 | Baker |
| 2008/0167540 A1 | 7/2008 | Korhonen et al. |
| 2008/0200775 A1 | 8/2008 | Lynn |
| 2008/0228052 A1* | 9/2008 | Al-Ali .................. 600/323 |
| 2009/0118630 A1 | 5/2009 | Li |
| 2009/0247837 A1 | 10/2009 | Ochs et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0286495 A1 | 11/2010 | McGonigle |
| 2011/0066062 A1 | 3/2011 | Banet et al. |
| 2011/0071406 A1 | 3/2011 | Addison et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2010/030238 A1 | 3/2010 |
| WO | WO 2011/048592 A1 | 4/2011 |

OTHER PUBLICATIONS

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

International Search Report and Written Opinion of the International Searching Authority for Application No. PCT/US2012/066188, mailed on Mar. 14, 2013. 6 pages.

Suzuki T. et al. Development of the irregular pulse detection method in daily life using wearable photoplethysmographic sensor. Conf Proc IEEE Eng Med Biol Soc, 2009;6080-3.

* cited by examiner

SYSTEMS AND METHODS FOR DETECTING ARRHYTHMIA FROM A PHYSIOLOGICAL SIGNAL

The present disclosure relates to physiological signal processing, and more particularly relates to detecting arrhythmia from a physiological signal.

SUMMARY

A patient monitoring system may be configured to determine physiological information such as respiration information from a physiological signal such as a photoplethysmograph (PPG) signal. For example, a PPG signal may exhibit amplitude and frequency modulation based on the respiration of a patient. Arrhythmias may also impact a physiological signal such as a PPG signal, and in some instances may obscure the determination of the desired physiological information.

A patient monitoring system may receive a physiological signal such as a PPG signal. Derived value data sets that are indicative of arrhythmia may be extracted from the physiological signal and analyzed to determine arrhythmia features. The arrhythmia features may be combined and compared to one or more thresholds to generate an arrhythmia indicator. The arrhythmia indicator may indicate that an arrhythmia has been detected, e.g., by generating a confidence value. The patient monitoring system may utilize the confidence value for further processing of the physiological information.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
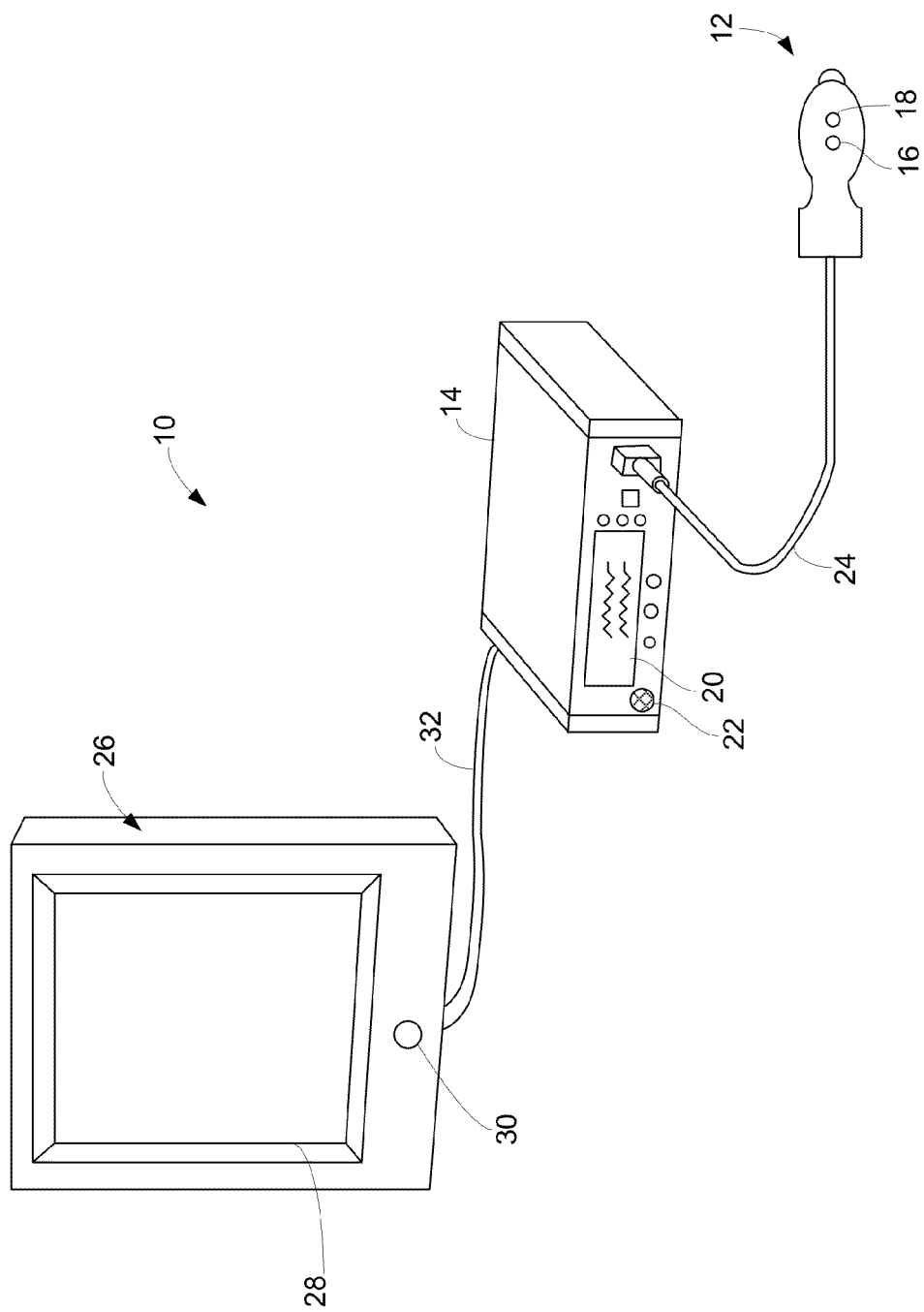
FIG. 1 shows an illustrative patient monitoring system in accordance with some embodiments of the present disclosure.

The present disclosure is directed towards detecting arrhythmia from a physiological signal. A patient monitoring system may receive one or more physiological signals, such as a photoplethysmograph (PPG) signal generated by a pulse oximeter sensor coupled to a patient. The patient monitoring system may extract physiological and morphology derived value data sets from the physiological signal such as pulse rate data set, a kurtosis derived value data set, and a b/a ratio derived value data set.

The derived value data sets may be utilized to calculate arrhythmia features. Arrhythmia features may include, for example, a standard deviation feature based on the pulse rate data set, an entropy feature calculated from the pulse rate data set, a dot product feature calculated from the kurtosis data set and the b/a ratio data set, any other suitable derived value data set, or any combination thereof. A relationship between the arrhythmia features and whether arrhythmia is present may be determined based on a learning algorithm. Suitable calculations may be performed on the arrhythmia features to generate an arrhythmia indicator. In some embodiments, the arrhythmia indicator may be based on the arrhythmia features, a set of weighting values associated with the arrhythmia features, and a bias value. In an exemplary embodiment, these values may be input to a trained neural net.

The arrhythmia indicator may be generated by decision logic which may detect arrhythmia. In some embodiments, the arrhythmia indicator may be a confidence value that varies between a "non-arrhythmia" value (e.g., 1) and an "arrhythmia" value (e.g., 0). Confidence values falling between 0 and 1 may indicate a relative likelihood of the presence of arrhythmia. In an exemplary embodiment, the decision logic may be implemented with fuzzy logic.

In some embodiments, a confidence value between 0 and 1 may indicate the relative likelihood that a particular type of arrhythmia is present (and therefore more or less likely to impact the calculation of a particular physiological parameter such as respiration rate). In an exemplary embodiment, some arrhythmias (e.g., respiratory sinus arrhythmia or isolated premature ventricular contraction) may result in a confidence value closer to 1 (i.e., non-arrhythmia) while others (e.g., atrial fibrillation or frequent premature ventricular contraction) may result may result in a confidence value closer to 0 (i.e., arrhythmia).

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows:

1. The natural logarithm of Eq. 1 is taken ("log" will be used to represent the natural logarithm) for IR and Red to yield $$\log I = \log I_o - (s\beta_o + (1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (11)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R,$$

which defines a cluster of points whose slope of y versus x will give R when $$x=I(t_2,\lambda_{IR})-I(t_1,\lambda_{IR})I(t_1,\lambda_R), \quad (12)$$

and $$y=[(t_2,\lambda_R)-I(t_1,\lambda_R)I](t_1,\lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters, e.g., a general purpose computer, tablet computer, smart phone, or an application-specific device. Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26, e.g., a keyboard, one or more buttons, a camera, or a touchpad.

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed and used by Covidien of Mansfield, Mass. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
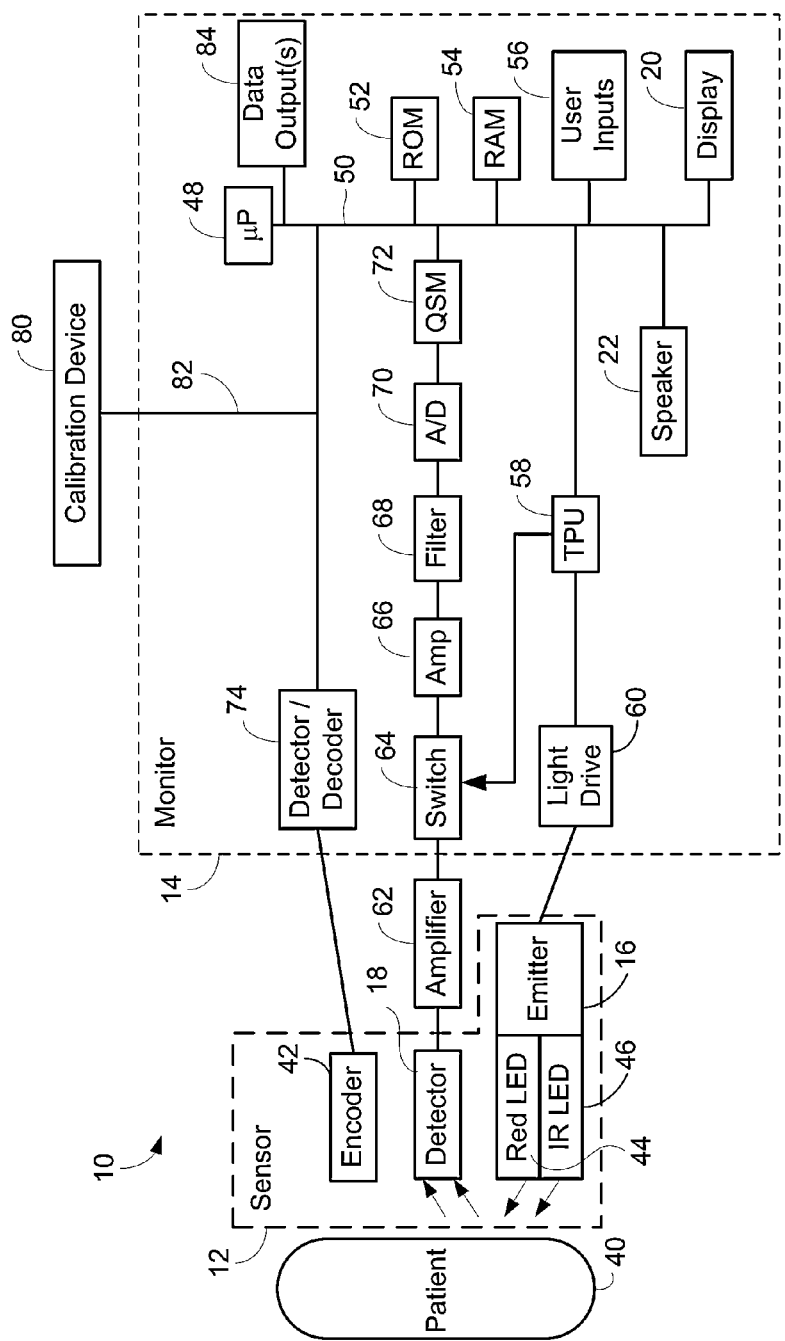
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
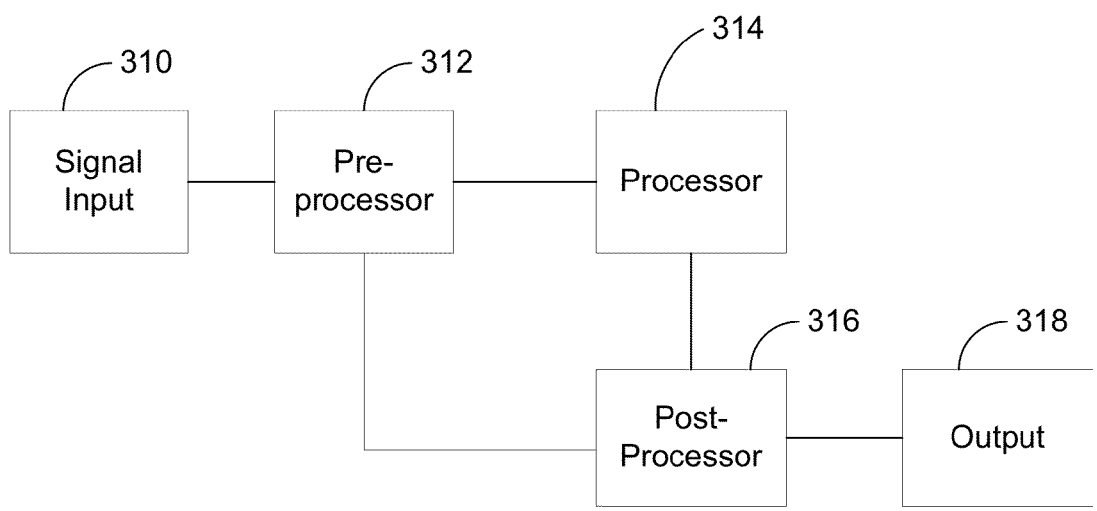
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In some embodiments, processing system 300 may be included in monitor 14 and/or display monitor 26 of a patient monitoring system (e.g., patient monitoring system 10 of FIGS. 1-2). In the illustrated embodiment, input signal 310 may be a PPG signal. Input signal 310 may be a PPG signal that was sampled and generated at monitor 14, for example at 76 Hz. Input signal 310, pre-processor 312, processor 314, and post-processor 316 may reside entirely within a single device (e.g., monitor 14 or display monitor 26) or may reside in multiple devices (e.g., monitor 14 and display monitor 26).

Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window, e.g., every 5 seconds. The received signal may include the PPG signal as well as other information related to the PPG signal, e.g., a pulse found indicator, the mean pulse rate from the PPG signal, the most recent pulse rate, an indicator for the most recent invalid sample, and an indicator of the last artifact for the PPG signal. It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof.

Other signal processing operations may be performed by pre-processor 312 and may be related to producing morphology metrics suitable as inputs to determine physiological information. Pre-processor 312 may perform calculations based on an analysis window of a series of recently received PPG signal sampling windows, e.g., a 45-second analysis window may correspond to the 9 most recent 5-second sampling windows. The physiological information may be respiration information, which may include any information relating to respiration, e.g., respiration rate, change in respiration rate, breathing intensity, etc.

Because respiration has an impact on pulse characteristics, it may be possible to determine respiration information from a PPG signal. However, other physiological phenomena such as certain arrhythmias may also have an impact on pulse characteristics. Exemplary arrhythmia types that may impact pulse characteristics include respiratory sinus arrhythmia ("RSA"), atrial fibrillation ("AF"), and premature ventricular contraction ("PVC"). In some instances the impact of arrhythmia on the PPG signal may make it difficult to determine a desired physiological parameter such as respiration information from the PPG signal. The impact of arrhythmia on the PPG signal may be based on the arrhythmia type, magnitude, and frequency. For example, it may be possible to determine respiration information from a PPG signal despite RSA or occasional PVC, while AF or frequent PVC may interfere with determining respiration information from a PPG signal.

Morphology metrics may be parameters that may be calculated from the PPG signal that provide information related to long term modulations or short term modulations of the PPG signal based on physiological phenomena such as respiration or arrhythmia. Examples include a down metric for a pulse, kurtosis for a pulse, the delta of the second derivative ("DSD") between consecutive pulses, the up metric for a pulse, skew, b/a ratio, c/a ratio, peak amplitude of a pulse, center of gravity of a pulse, or area of a pulse. Other information that may be determined by pre-processor 312 may include the pulse rate, the variability of the period of the PPG signal, the variability of the amplitude of the PPG signal, and an age measurement indicative of the age of the useful portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive any suitable physiological information and calculated parameters from pre-processor 312. For example, processor may receive a pulse rate value and morphology metrics for use in determining respiration information. Processor 314 may be coupled to post-processor 316 and may communicate any suitable information such as respiration information to post-processor 316. Pre-processor 312 may also provide any suitable information to post-processor 316. Post-processor 316 may utilize the received information to calculate and output any suitable physiological parameter such as respiration information. Post-processor 316 may provide the output information to output 318.

Processor 314, post-processor 316, or both, may determine any suitable physiological parameter. In an exemplary embodiment, processor 314, post-processor 316, or both may determine respiration information such as respiration rate. Respiration information such as respiration rate may be determined in any suitable manner. In an exemplary embodiment, a plurality of morphology metric signals may be generated based on the morphology metrics, as is described in more detail in co-pending, commonly assigned U.S. patent application Ser. No. 13/243,853, filed Sep. 23, 2011 (published as U.S. Patent Publication No. 2013/0079606 on Mar. 28, 2013) and entitled "SYSTEMS AND METHODS FOR DETERMINING RESPIRATION INFORMATION FROM A PHOTOPLETHYSMOGRAPH," which is incorporated by reference herein in its entirety. Respiration information may be determined based on the morphology metric signals in any suitable manner. In an exemplary embodiment, a corresponding autocorrelation sequence may be generated for each of the morphology metric signals, and respiration information may be determined based on the autocorrelation sequences. Autocorrelation sequences for determining respiration information may be generated in any suitable manner, such as is described in more detail in co-pending, commonly assigned U.S. patent application Ser. No. 13/243,951, filed Sep. 23, 2011 (published as U.S. Patent Publication No. 2013/0080489 on Mar. 28, 2013) and entitled "SYSTEMS AND METHODS FOR DETERMINING RESPIRATION INFORMATION FROM A PHOTOPLETHYSMOGRAPH," which is incorporated by reference herein in its entirety. Respiration information may then be determined from autocorrelation signals in any suitable manner. In an exemplary embodiment, respiration information may be determined directly from a combined autocorrelation sequence as is described in more detail in co-pending, commonly assigned U.S. patent application Ser. No. 13/243,785, filed Sep. 23, 2011 (published as U.S. Patent Publication No. 2013/0079656 on Mar. 28, 2013) and entitled "SYSTEMS AND METHODS FOR DETERMINING RESPIRATION INFORMATION FROM A PHOTOPLETHYSMOGRAPH," which is incorporated by reference herein in its entirety. In another exemplary embodiment, respiration information may be determined based on a continuous wavelet transform as is described in more detail in co-pending, commonly assigned U.S. patent application Ser. No. 13/243,892, filed Sep. 23, 2011 (published at U.S. Patent Publication No. 2013/0079657 on Mar. 28, 2013) and entitled "SYSTEMS AND METHODS FOR DETERMINING RESPIRATION INFORMATION FROM A PHOTOPLETHYSMOGRAPH," which is incorporated by reference herein in its entirety.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, arrhythmia features, arrhythmia indicators, confidence values, or other information corresponding to physiological monitoring.

It will be understood that system 300 may be incorporated into system 10 (FIGS. 1 and 2) in which, for example, input signal 310 may be generated by sensor unit 12 (FIGS. 1 and 2), monitor 14 (FIGS. 1 and 2), or both. Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, infrared, or any other suitable transmission scheme. In some embodiments, a wireless transmission scheme may be used between any communicating components of system 300.

Respiratory activities may cause particular changes in the morphology of a PPG signal throughout a respiratory cycle, including, for example, on a pulse by pulse basis. In some circumstances, these changes in morphology may be in addition to morphological change due to arrhythmia, changes in stroke volume, pulse rate, blood pressure, any other suitable physiological parameters, or any combination thereof. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. Morphology metrics may be calculated on any portion of a PPG signal, but in one exemplary embodiment each consecutive set of fiducial points may define a relevant portion of the PPG signal for calculating a morphology metric, and may be referred to herein as a fiducial-defined portion. Fiducial points for a PPG signal may be determined in any suitable manner, such as is described in more detail in co-pending, commonly assigned U.S. patent application Ser. No. 13/243,907, filed Sep. 23, 2011 (published as U.S. Patent Publication No. 2013/0079647) and entitled "SYSTEMS AND METHODS FOR DETERMINING RESPIRATION INFORMATION FROM A PHOTOPLETHYSMOGRAPH," which is incorporated by reference herein in its entirety.

Figure 4:
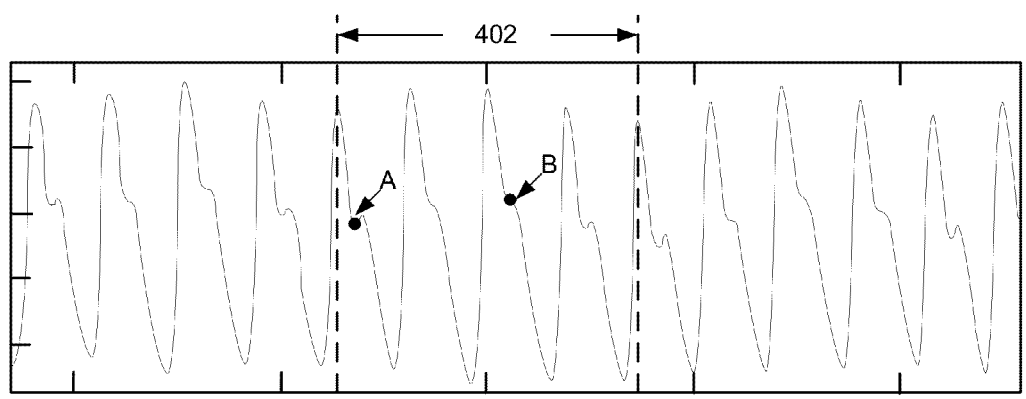
FIG. 4 shows an illustrative PPG signal that may be analyzed in accordance with some embodiments of the present disclosure.
Figure 5:
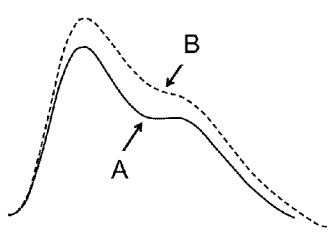
FIG. 5 shows an illustrative PPG signal having morphology characteristics relating to respiration in accordance with some embodiments of the present disclosure.

An example of a PPG signal changing its morphology over a series of pulse cycles associated with a respiratory cycle is depicted in FIG. 4 and FIG. 5. A respiratory cycle may typically have a longer period (lower frequency) than a pulse cycle and may span a number of pulse periods. A respiratory cycle may span a number of pulse cycles based on the relative respiration rate and pulse rate. An exemplary respiratory cycle 402 may span four pulse periods as depicted in FIG. 4. Respiration may impact the shape of the pulse waveform, e.g., by amplitude and frequency modulation. For example, as depicted in FIG. 5, a first pulse associated with the respiratory cycle may have a relatively low amplitude as well as an obvious distinct dichrotic notch as indicated by point A. A second pulse may have a relatively high amplitude as well as a dichrotic notch that has been washed out as depicted by point B. FIG. 5 depicts the pulses associated with point A and B superimposed on the same scale for comparison. By the end of the respiratory cycle the pulse features may again be similar to the morphology of A. Respiration may have varied effects on the morphology of a PPG signal other than those depicted in FIG. 5.

A PPG signal may also change its morphology when arrhythmia is present. In some instances it may be desirable to detect arrhythmia to assist in determining physiological information based on morphology. For example, it may be difficult to distinguish morphology changes due to respiration from certain morphology changes due to arrhythmia, e.g., based on the type of arrhythmia, the magnitude of the arrhythmia, and the frequency of the arrhythmia. In some embodiments suitable processing may be performed based on the detection of arrhythmia, e.g., to more accurately calculate a physiological parameter such as respiration information.

Figure 6:
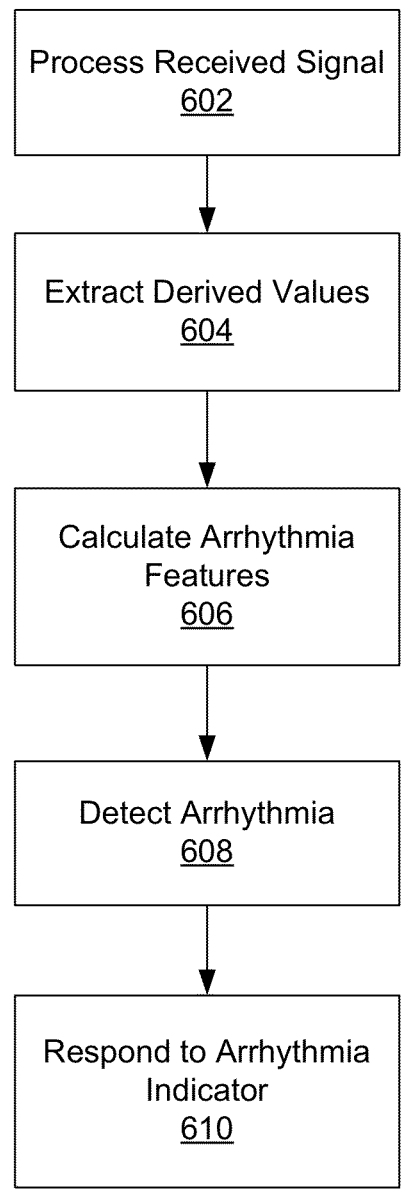
FIG. 6 is a flow diagram showing illustrative steps for detecting arrhythmia in accordance with some embodiments of the present disclosure.

FIG. 6 depicts steps 600 for detecting arrhythmia from a physiological signal such as a PPG signal in accordance with some embodiments of the present disclosure. Although an exemplary embodiment is described herein, it will be understood that each of steps 600 may be performed by pre-processor 312, processor 314, post-processor 316, or any combination thereof. It will also be understood that steps 600 may be performed in alternative sequence or in parallel, that steps may be omitted, and that additional steps may be added or inserted.

At step 602 pre-processor 312 may process a received signal such as a PPG signal. Processing the received signal may include any suitable processing steps useful to prepare the PPG signal to be analyzed for arrhythmia, such as establishing fiducial points, filtering the PPG signal, and identifying any problematic portions of the PPG signal. Examples of problematic portions of the PPG signal may be portions (as well as surrounding portions) that demonstrate a large baseline shift, the presence of motion artifacts, large pulse period variability, or an out of range pulse rate. Any problematic portions of the signal may be discarded, filtered, zeroed out, or otherwise processed in any suitable manner.

At step 604 pre-processor 312 may extract one or more derived values for an analysis window to generate one or more derived value data sets. Derived value data sets are described herein in terms of derived values signals for clarity and brevity. Extracted derived values may include any suitable derived values for detecting arrhythmia from the received signal, such as pulse rate, morphology metrics, a FM demodulated PPG signal, any other suitable derived value, or any combination thereof. Each resulting derived value signal may consist of a sequence of samples determined in any suitable manner, e.g., at a set sampling rate, based on a pulse rate, or for each fiducial-defined portion of the analysis window. Any number of derived value signals may be determined from the PPG signal. Any suitable aspect of a FM demodulated signal may be used as a derived value for detecting arrhythmia, such as the magnitude of the FM demodulated signal. Any suitable morphology metric may be used as a derived value for detecting arrhythmia, such as a down metric, kurtosis metric, DSD derivative metric, or b/a ratio metric.

The down metric is the difference between a first (e.g., fiducial) sample of a fiducial-defined portion of the PPG signal and a minimum sample of the fiducial-defined portion of the PPG signal. The DSD metric is the delta (difference) between fiducial points in consecutive fiducial-defined portions of the second derivative of the PPG signal.

The PPG signal may include a number of peaks (e.g., four peaks corresponding to maxima and minima) which may be described as the a-peak, b-peak, c-peak, and d-peak, with the a-peak and c-peak generally corresponding to local maxima within a fiducial-defined portion and the b-peak and d-peak generally corresponding to local minima within a fiducial-defined portion. For example, the PPG signal (or a signal derived from the PPG signal) may include four peaks: the a-peak, b-peak, c-peak, and d-peak. Each peak may be indicative of a respective systolic wave, i.e., the a-wave, b-wave, c-wave, and d-wave. The b/a ratio metric is based on the ratio between the b-peak and a-peak of the PPG signal (i.e., b/a), e.g., in the second derivative.

Kurtosis measures the peakedness of a signal, such as the PPG signal, a first or second derivative of the PPG signal, or other derived value signals. In an exemplary embodiment a kurtosis metric may be based on the first derivative of the PPG signal. The kurtosis of a signal may be calculated based on the following formulae:

$$D = \frac{1}{n}\sum_{i=1}^{n}(x'_i - \bar{x}')^2 \quad (14)$$

$$\text{Kurtosis} = \frac{1}{nD^2}\sum_{i=1}^{n}(x'_i - \bar{x}')^4 \quad (15)$$

where:
$x_i'$=ith sample of $1^{st}$ derivative;
n=set of all samples in the fiducial-defined portion At step 606 processor 314 may calculate one or more arrhythmia features based on the one or more derived value signals received from pre-processor 312. The arrhythmia features may be the result of any suitable calculations such as a standard deviation, entropy, kurtosis, and dot product. Any number of arrhythmia features may be calculated from a single derived value signal and any combination of derived values signals may be utilized as inputs to determine a single arrhythmia feature. Each arrhythmia feature may provide an indication of the presence and/or type of arrhythmia, based on the underlying derived value data set and the calculation performed. For example, the standard deviation may be indicative of the variation of an underlying derived value over an analysis window, entropy may indicate the randomness of an underlying derived value over an analysis window, the dot product may be indicative of similarity or difference in the phase of the derived values over an analysis window, and kurtosis may be sensitive to changes in both frequency and magnitude over an analysis window. Exemplary arrhythmia features include the standard deviation of the pulse rate, the entropy of the pulse rate, the dot product of the kurtosis metric and the b/a ratio metric, the kurtosis of the pulse rate, the standard deviation of the down metric, the entropy of the down metric, the kurtosis of the down metric, the standard deviation of the kurtosis metric, the entropy of the kurtosis metric, the kurtosis of the kurtosis metric, the standard deviation of the DSD metric, the entropy of the DSD metric, the kurtosis of the DSD metric, the standard deviation of the FM demodulated PPG signal, the entropy of the FM demodulated PPG signal, the kurtosis of the FM demodulated PPG signal, and any other suitable calculation based on a derived value signal.

At step 608 processor 314 may detect arrhythmia based on the one or more arrhythmia features. Each arrhythmia feature may provide some information relating to the presence of arrhythmia based on the underlying derived value or derived values used to generate the derived value signal and the calculations used to generate the arrhythmia feature. An arrhythmia indicator may be generated from the one or more arrhythmia features in any suitable manner. In an exemplary embodiment, a learning algorithm such as a perceptron algorithm may be used to determine which combination of derived value signals and calculation methods best detect arrhythmia or distinguish between arrhythmias based on training data. A resulting arrhythmia classifier/detector may use any kind of linear or nonlinear classifiers based on input features. The output of such a classifier/detector is used to generate an arrhythmia result used to determine an arrhythmia indicator. The resulting weights, bias value, and arrhythmia features may be inputs into a trained neural net. Fuzzy logic may also be used to implement the decision logic.

The arrhythmia indicator may be indicative of the presence of arrhythmia (e.g., an indicator of "arrhythmia" vs. "no arrhythmia"), of a classification of arrhythmia (e.g., an indicator of "good arrhythmia" vs. "bad arrhythmia"), or a type of arrhythmia (e.g., an indicator of RSA, PVC, or AF). The arrhythmia indicator may be in any form, such as a binary value or a range indicating a confidence level. For example, an exemplary arrhythmia indicator may be a confidence value based on a soft thresholding logic, with arrhythmia result values exceeding a first threshold resulting in a "1" (indicative of no arrhythmia), arrhythmia result values falling below a second threshold resulting in a "0" (indicative of arrhythmia), and arrhythmia result values falling between the first and second threshold having a value indicative of the likelihood of arrhythmia.

At step 610 processor 314 may respond based on the arrhythmia indicator. Exemplary responses may be to display or communicate the presence of arrhythmia, display or communicate a type of arrhythmia, modify the calculation of a physiological parameter based on the arrhythmia indicator, change a weighting factor for the most recent value of a physiological parameter based on the arrhythmia indicator, block processor 314 from calculating a physiological parameter when arrhythmia is present, block the display of a physiological parameter when arrhythmia is present, or perform any other suitable operation based on the arrhythmia indicator.

Figure 7A:
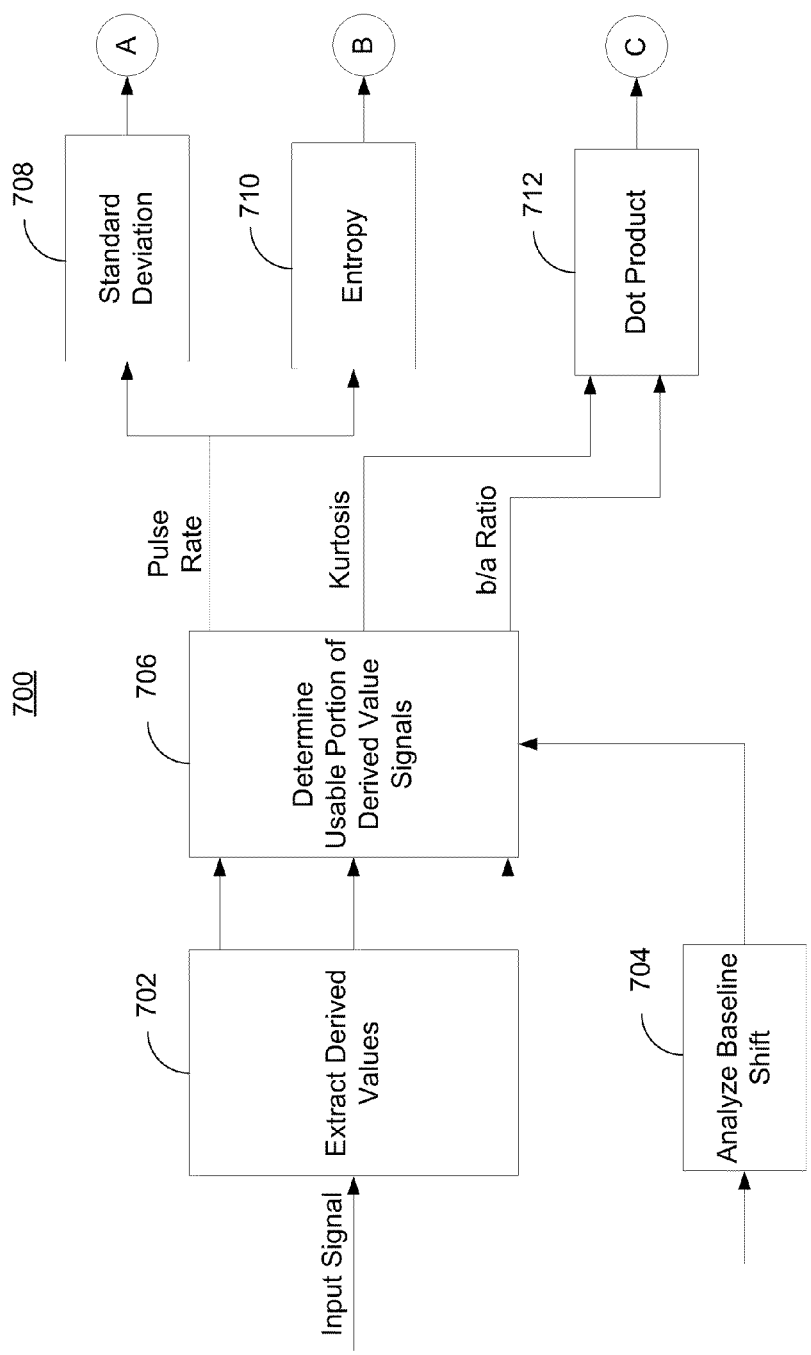
FIG. 7A is a flow diagram showing illustrative steps for determining exemplary arrhythmia features in accordance with some embodiments of the present disclosure.
Figure 7B:
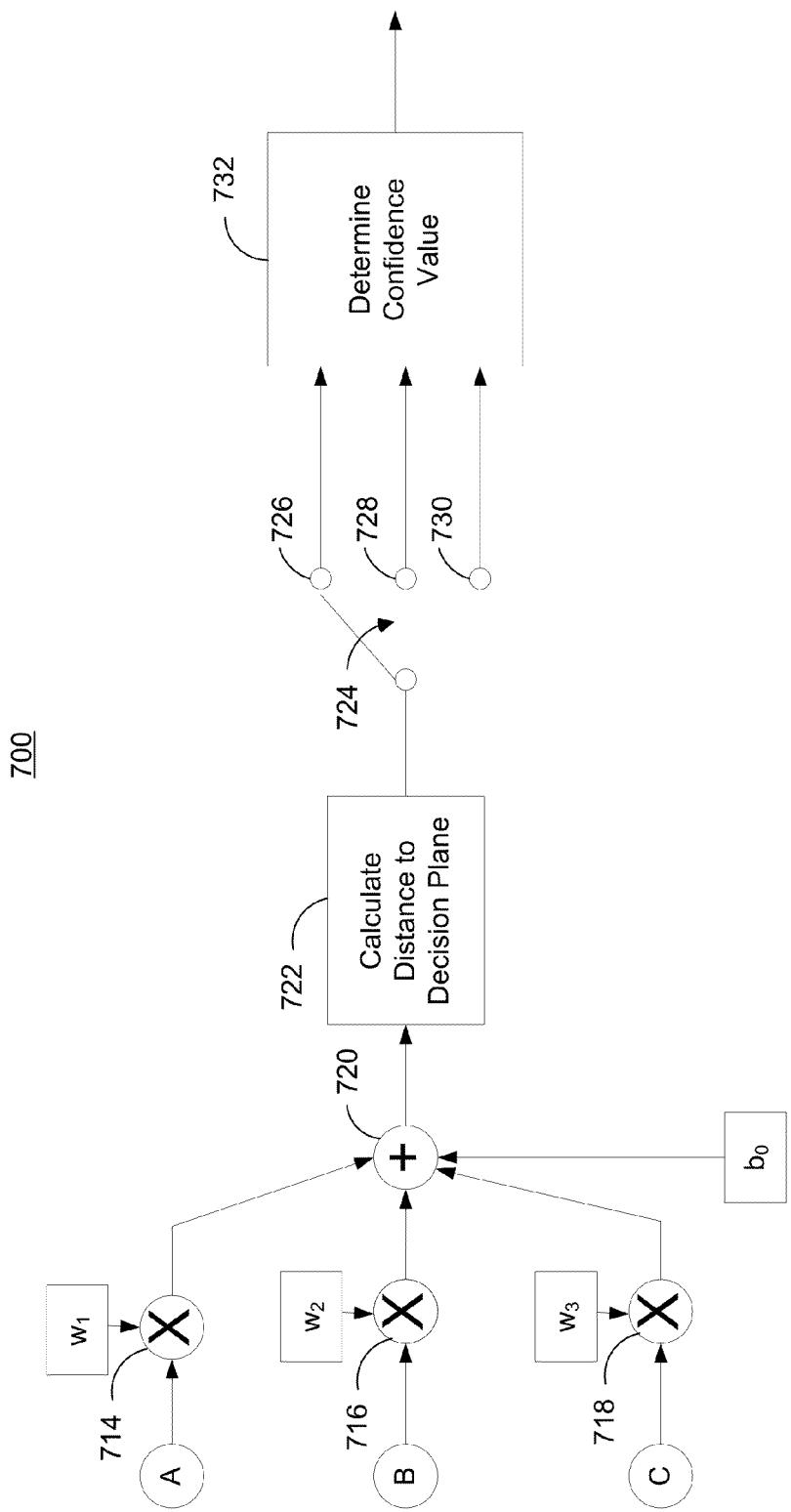
FIG. 7B is a flow diagram showing illustrative steps for determining an exemplary arrhythmia indicator in accordance with some embodiments of the present disclosure.

FIGS. 7A and 7B depict steps 700 for detecting arrhythmia from a PPG signal in accordance with some embodiments of the present disclosure. It will be understood that steps described herein are exemplary, and that some or all of the steps herein may be omitted, additional steps may be added, and the order of the steps may be modified in any suitable manner. It will further be understood that the particular derived value signals, arrhythmia features, arrhythmia indicators, and the steps described herein are exemplary only and may be modified in any suitable manner, e.g., as described herein with respect to FIG. 6. It will be understood that the each of the steps herein may be performed by pre-processor 312, processor 314, post-processor 316, or any combination thereof.

An input signal may be a PPG signal encompassing an analysis window, e.g., a 45 second analysis window. At step 702, pre-processor 312 may extract any suitable derived value signals from the PPG signal, such as a pulse rate signal, a kurtosis metric signal, and a b/a ratio metric signal. The pulse rate signal may be a sequence of samples indicating the change in the pulse rate over the analysis period, e.g., based on the pulse period. The kurtosis metric signal and b/a ratio metric signal may each be a sequence of samples wherein each respective metric value is calculated for each fiducial-defined portion within the analysis window.

At step 704 pre-processor 312 may determine whether to exclude any portions of the PPG signal from analysis by the arrhythmia detector. In an exemplary embodiment, pre-processor 312 may analyze a baseline shift of the PPG signal. A large baseline shift may be indicative of a motion artifact or other artificial change in the signal baseline. A baseline shift may be detected in any suitable manner, such as is described in more detail in co-pending, commonly assigned U.S. patent application Ser. No. 13/243,853, filed Sep. 23, 2011 and entitled "SYSTEMS AND METHODS FOR DETERMINING RESPIRATION INFORMATION FROM A PHOTOPLETHYSMOGRAPH," which was incorporated by reference herein in its entirety above. At step 706 pre-processor 312 may determine the usable portion of the derived value signals based on the baseline shift output of step 704. The usable portion may be determined in any suitable manner, such as excluding any portion of the derived value signals that occur prior to the occurrence of the baseline shift within the analysis window. The resulting derived value signals, adjusted for any large baseline shift, may be output to processor 314.

Arrhythmia features may be calculated from the derived value signals at steps 708, 710, and 712. It will be understood that one or more arrhythmia features may be determined in any suitable manner, and that any number of derived values may be used to calculate arrhythmia features. In an exemplary embodiment processor 314 may determine a standard deviation arrhythmia feature, an entropy arrhythmia feature, and a dot product arrhythmia feature. At step 708 processor 314 may determine a standard deviation arrhythmia feature based on the pulse rate derived value signal. For a sequence of N samples of the pulse rate derived value signal, a standard deviation arrhythmia feature may be calculated as follows:

$$std = \sqrt{\frac{1}{N-1}\sum_{i=1}^{N}(x_i - \bar{x})^2} \quad (16)$$

where:
std=standard deviation;
N=number of samples;
$x_i$=pulse rate for sample i; and
$\bar{x}$=mean pulse rate for the analysis window.

At step 710 processor 314 may determine an entropy arrhythmia feature based on the pulse rate derived value signal. A set of M evenly spaced bins may be allocated to cover a given pulse rate range, and each pulse rate sample may be assigned to a corresponding bin. In an example embodiment, 20 evenly spaced bins may be allocated to a pulse rate range of 20-250 beats per minute. A probability distribution may be calculated for each of the M bins as follows:

$$P_i = \frac{\#\_of\_pulses}{N} \quad (17)$$

where:
$P_i$=probability distribution for bin i;
N=total number of samples in sampling window; and
_of_pulses=number of pulses with a pulse rate in the i-th bin.

The entropy arrhythmia feature may be calculated from the probability distribution as follows:

$$e = -\sum_{i=1}^{M} P_i \log P_i \quad (18)$$

where:
e=entropy arrhythmia feature; and
M=number of bins.

At step 712 processor 314 may determine a dot product arrhythmia feature based on the kurtosis derived value signal and the b/a ratio derived value signal. The kurtosis derived value and b/a ratio derived value may show a relatively strong correlation for a normal physiological signal, but a weaker correlation when an arrhythmia such as PVC is present. The dot product arrhythmia feature may be calculated as follows:

$$DP = \frac{1}{N}\sum_{i=1}^{N}(kur_i \cdot baRatio_i) \quad (19)$$

where:
DP=dot product arrhythmia feature;
N=number of samples;
$kur_i$=kurtosis value for sample i; and
$baRatio_i$=b/a ratio value for sample i.

Referring to FIG. 7B, the calculated arrhythmia features may be used to determine an arrhythmia indicator. In an exemplary embodiment, the arrhythmia features may be inputs to a linear classifier or other type of linear or nonlinear classifiers such as neural networks for determining the arrhythmia indicator. At step 714 the standard deviation arrhythmia feature may be multiplied by weight $w_1$ (i.e., $w_{std}$), at step 716 the entropy arrhythmia feature may be multiplied by weight $w_2$ (i.e., $w_e$), and at step 718 the dot product arrhythmia feature may be multiplied by weight $w_3$ (i.e., $w_{DP}$). Each of weights $w_1$, $w_2$, and $w_3$ may be determined in any suitable manner, such as based on a learning algorithm. At step 720 the weighted arrhythmia features may be combined with a bias value $b_0$, which may be determined in any suitable manner such as a based on a learning algorithm. At step 722, a distance to the decision plane (decision value) d may be calculated from the output of step 720 based on the following:

$$d = \frac{w_{std}x_{std} + w_e x_e + w_{DP}x_{DP} + b_0}{\|W\|} \quad (20)$$

where:
d=distance to decision plane;
$w_{std}$=standard deviation weight;
$x_{std}$=standard deviation arrhythmia feature;
$w_e$=entropy weight;
$x_{std}$=entropy arrhythmia feature;
$w_{DP}$=dot product weight;
$x_{DP}$=dot product arrhythmia feature;
$b_0$=bias value; and
$\|W\|$=norm of the vector $W=[w_{std}\ w_e\ w_{DP}]^T$.

At step 724 the decision value d may be compared to a threshold distance $d_0$ based on soft thresholding logic. In an exemplary embodiment, if $d \geq d_0$, an arrhythmia indicator 726 of "1" may be indicative of no arrhythmia, or in some embodiments, of a good arrhythmia that is not expected to interfere with the calculation of a physiological parameter such as respiration rate. If $d \leq -d_0$, an arrhythmia indicator 730 of "0" may be indicative of arrhythmia, or in some embodiments, of a bad arrhythmia that may interfere with the calculation of a physiological parameter such as respiration rate. If $-d_0 < d < d_0$, an arrhythmia indicator 728 may be indicative of a possible or mild arrhythmia. At step 732 a confidence value may be determined. The confidence value may correspond to the arrhythmia indicator if the arrhythmia indicator is 1 or 0. If $-d_0 < d < d_0$, a confidence value (e.g., between 1 and 0) may be calculated at step 732 using soft thresholding as follows:

$$f(d) = \frac{d}{2d_0} + 1/2 \quad (21)$$

where:
f(d)=confidence value;
d=distance to decision plane; and
$d_0$=threshold distance.

The resulting confidence value of 1, 0, or f(d) may be utilized by processor 314 or post-processor 316 for the processing of physiological information such as respiration information. Exemplary responses may be to display or communicate the presence of arrhythmia, display or communicate a type of arrhythmia, modify the calculation of the physiological parameter based on the arrhythmia indicator, change a weighting factor for the most recent value of the physiological parameter based on the arrhythmia indicator, block processor 314 from calculating the physiological parameter when arrhythmia is present, block the display of the physiological parameter when arrhythmia is present, or perform any other suitable operation based on the arrhythmia indicator. In an exemplary embodiment a current value of the physiological information that corresponds to the current analysis window may not be displayed if the confidence value is 0, while a confidence value between 0 and 1 (i.e., f(d)) may result in the current value being averaged with historical values based on a weighting factor that corresponds to the confidence value.

Figure 8:
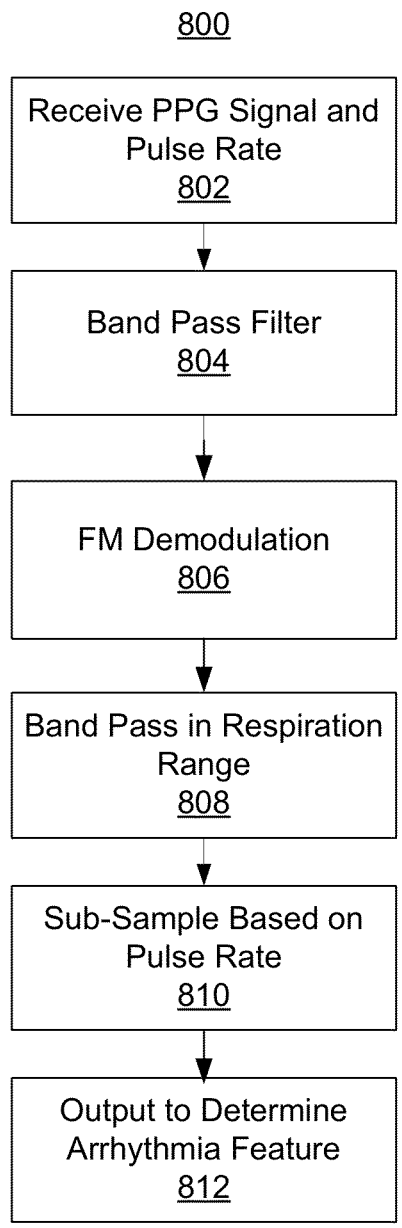
FIG. 8 is a flow diagram showing illustrative steps for generating a FM demodulated derived value data set in accordance with some embodiments of the present disclosure.

FIG. 8 depicts steps for using frequency demodulation to determine a derived value signal in accordance with some embodiments of the present disclosure. The steps depicted in FIG. 8 may be performed by pre-processor 312, processor 314, post-processor 316, or any combination thereof. It will also be understood that steps 800 may be performed in alternative sequence or in parallel, that steps may be omitted, and that additional steps may be added or inserted.

Figure 9:
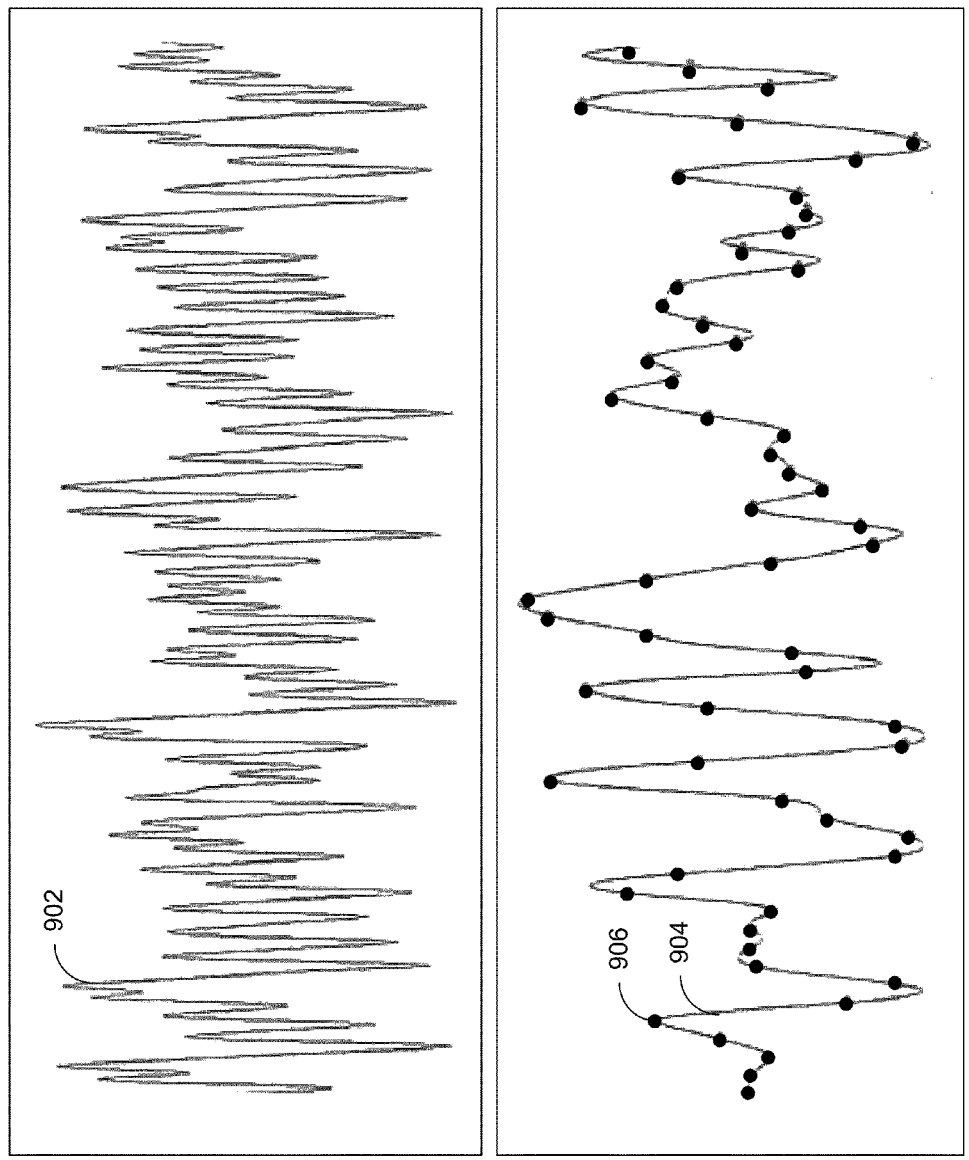
FIG. 9 shows an illustrative PPG signal and FM demodulated derived value data set in accordance with some embodiments of the present disclosure.

At step 802 pre-processor 312 may receive a PPG signal spanning an analysis window as well as a calculated pulse rate for the analysis window. An exemplary PPG signal is depicted in FIG. 9 as PPG signal 902. At step 804 the PPG signal may be band pass filtered based on the pulse rate to remove frequency information outside of a window of interest. In an exemplary embodiment a band pass filter may be from 0.1 to 1.9 times the pulse rate. At step 806 the resulting band pass filtered PPG signal may be FM demodulated in any suitable manner, e.g., to resolve aliasing issues in the underlying PPG signal. At step 808 the resulting FM demodulated signal may be band pass filtered about a region of interest for respiration, e.g., within a frequency window corresponding to 3-40 breaths per minute. An exemplary resulting signal is depicted in FIG. 9 as signal 904. At step 810 the resulting signal may be subsampled based on the pulse rate, as is depicted by sampling points 906 of FIG. 9. At step 812 the samples may be output as a FM demodulated derived value signal for use in determining one or more arrhythmia features as described herein, e.g., by determining the entropy or standard deviation of the FM demodulated derived value signal.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:
1. A method for detecting arrhythmia from a plethysmograph signal, the method comprising:
   extracting, using processing equipment, a plurality of derived value data sets associated with the plethysmograph signal;
   determining, using processing equipment, a plurality of arrhythmia features based on the derived value data sets, wherein the arrhythmia features comprise an entropy feature;

generating, using processing equipment, an arrhythmia indicator based on the arrhythmia features; and determining respiration information based on the arrhythmia indicator.

2. The method of claim 1, wherein the derived value data sets comprise at least one of a pulse rate data set, a kurtosis data set, and a b/a ratio data set.

3. The method of claim 1 wherein the arrhythmia features further comprise a standard deviation feature.

4. The method of claim 1 wherein the arrhythmia features further comprise a dot product feature.

5. The method of claim 1, wherein generating the arrhythmia indicator comprises:

calculating a distance value based on the plurality of arrhythmia features;

comparing the distance value to a threshold distance value; and generating the arrhythmia indicator based on the distance value and the threshold distance value.

6. The method of claim 5 wherein comparing the distance value comprises determining whether the distance value falls within a range of values based on the threshold distance value.

7. The method of claim 6 wherein the range of values is less than a positive threshold distance value and greater than a negative threshold distance value.

8. The method of claim 5 wherein calculating the distance value comprises:

modifying each of the plurality of arrhythmia features based on one or more weighting factors; and calculating the distance value based on the modified arrhythmia features and a bias term.

9. The method of claim 1 wherein generating the arrhythmia indicator comprises determining a confidence value.

10. A patient monitoring system comprising:

an interface configured to receive a plethysmograph signal; and a processor configured to:

extract a plurality of derived value data sets associated with the plethysmograph signal;

determine a plurality of arrhythmia features based on the derived value data sets, wherein the arrhythmia features comprise an entropy feature;

generate an arrhythmia indicator based on the arrhythmia features; and determine respiration information based on the arrhythmia indicator.

11. The patient monitoring system of claim 10, wherein the derived value data sets comprise at least one of a pulse rate data set, a kurtosis data set, and a b/a ratio data set.

12. The patient monitoring system of claim 10 wherein the arrhythmia features further comprise a standard deviation feature.

13. The patient monitoring system of claim 10 wherein the arrhythmia features further comprise a dot product feature.

14. The patient monitoring system of claim 10, wherein the processor is further configured to:

calculate a distance value based on the plurality of arrhythmia features;

compare the distance value to a threshold distance value; and generate the arrhythmia indicator based on the distance value and the threshold distance value.

15. The patient monitoring system of claim 14 wherein the processor is further configured to determine whether the distance value falls within a range of values based on the threshold distance value.

16. The patient monitoring system of claim 15 wherein the range of values is less than a positive threshold distance value and greater than a negative threshold distance value.

17. The patient monitoring system of claim 14 wherein the processor is further configured to:

modify each of the plurality of arrhythmia features based on one or more weighting factors; and calculate the distance value based on the modified arrhythmia features and a bias term.

18. The patient monitoring system of claim 10 wherein the arrhythmia indicator comprises an arrhythmia confidence value.

19. A patient monitoring system comprising:

an interface configured to receive a plethysmograph signal; and a processor configured to:

extract a plurality of derived value data sets associated with the plethysmograph signal;

determine a plurality of arrhythmia features based on the derived value data sets, wherein the arrhythmia features comprise an entropy feature;

calculate a distance value based on the plurality of arrhythmia features;

compare the distance value to a threshold distance value; and generate an arrhythmia indicator based on the distance value and the threshold distance value.

* * * * *